US008173367B2

(12) United States Patent
Boucher et al.

(10) Patent No.: US 8,173,367 B2
(45) Date of Patent: May 8, 2012

(54) *IN SITU* DILUTION OF EXTERNAL CONTROLS FOR USE IN MICROARRAYS

(76) Inventors: Sherri Boucher, Ottawa (CA); Craig Parfett, Ottawa (CA); Carole Yauk, Ottawa (CA); Andrew Williams, Ottawa (CA); George R. Douglas, Kanata (CA); Gu Zhou, Kanata (CA)

( * ) Notice: Subject to any disclaimer, the term of this patent is extended or adjusted under 35 U.S.C. 154(b) by 1182 days.

(21) Appl. No.: 11/253,987

(22) Filed: Oct. 18, 2005

(65) Prior Publication Data
US 2006/0115840 A1    Jun. 1, 2006

Related U.S. Application Data

(60) Provisional application No. 60/619,008, filed on Oct. 18, 2004.

(51) Int. Cl.
*C12Q 1/68* (2006.01)
*C12M 1/00* (2006.01)
*C12M 1/34* (2006.01)
*C12M 3/00* (2006.01)

(52) U.S. Cl. .... 435/6.1; 435/283; 435/287.1; 435/287.2
(58) Field of Classification Search .................. None
See application file for complete search history.

(56) References Cited

U.S. PATENT DOCUMENTS

| | | | | |
|---|---|---|---|---|
| 5,976,893 A * | 11/1999 | Dennis et al. | ............... | 436/501 |
| 6,040,138 A * | 3/2000 | Lockhart et al. | ................ | 435/6 |
| 6,200,737 B1 * | 3/2001 | Walt et al. | .................... | 430/320 |
| 6,245,518 B1 | 6/2001 | Baier | | |
| 6,306,643 B1 | 10/2001 | Gentalen et al. | | |
| 6,408,308 B1 | 6/2002 | Maslyn et al. | | |
| 6,423,535 B1 | 7/2002 | Arnold et al. | | |
| 6,471,916 B1 * | 10/2002 | Noblett | ..................... | 422/82.08 |
| 6,490,533 B2 | 12/2002 | Weiner et al. | | |
| 6,492,122 B2 | 12/2002 | Weidenhammer et al. | | |
| 6,516,276 B1 | 2/2003 | Ghandour et al. | | |
| 6,571,005 B1 | 5/2003 | Li et al. | | |
| 6,620,625 B2 * | 9/2003 | Wolk et al. | ................... | 436/180 |
| 6,715,579 B1 | 4/2004 | Hendron | | |

(Continued)

FOREIGN PATENT DOCUMENTS

WO    WO 02/18655    3/2002

(Continued)

OTHER PUBLICATIONS

K. Almstrup et al., "Analysis of Cell-Type-Specific Gene Expression During Mouse Spermatogenesis", Biology of Reproduction 70, Feb. 2004, p. 1751-1761.

*Primary Examiner* — Robert T. Crow
(74) *Attorney, Agent, or Firm* — Robic

(57) ABSTRACT

An array in which an external control feature for normalization has been designed and tested for its ability to mimic the range of observed expression levels for a test set of oligos. The external control probes span a series of concentrations. They are spatially randomized across a grid of an array. The series of concentrations is duplicated in a given grid. The individual grid layout and number of control and external normalization features per grid have been designed to cope with sources of both systematic error and spatial variation.

36 Claims, 18 Drawing Sheets
(7 of 18 Drawing Sheet(s) Filed in Color)

U.S. PATENT DOCUMENTS

| | | |
|---|---|---|
| 6,759,197 B2 | 7/2004 | Wang |
| 2001/0026919 A1* | 10/2001 | Chenchik et al. ........... 435/6 |
| 2002/0009736 A1 | 1/2002 | Wang |
| 2002/0012932 A1 | 1/2002 | Wang |
| 2002/0150909 A1* | 10/2002 | Stuelpnagel et al. ........ 435/6 |
| 2003/0065449 A1 | 4/2003 | Wolber et al. |
| 2003/0148286 A1 | 8/2003 | Larose et al. |
| 2003/0186250 A1 | 10/2003 | Shah |
| 2003/0186310 A1 | 10/2003 | Kincaid |
| 2003/0215807 A1 | 11/2003 | Wolber et al. |
| 2003/0216870 A1 | 11/2003 | Wolber et al. |
| 2003/0226098 A1 | 12/2003 | Weng |
| 2004/0014040 A1 | 1/2004 | Mendrick et al. |
| 2004/0033485 A1 | 2/2004 | Li et al. |
| 2004/0043405 A1 | 3/2004 | Castle et al. |
| 2004/0048297 A1 | 3/2004 | Scherf |
| 2004/0072160 A1 | 4/2004 | Mendrick et al. |
| 2004/0142351 A1 | 7/2004 | Dozmorov et al. |

FOREIGN PATENT DOCUMENTS

| | | |
|---|---|---|
| WO | WO 02/099071 | 12/2002 |
| WO | WO 03/100422 | 12/2003 |
| WO | WO 2004/064482 | 8/2004 |

* cited by examiner

IN SITU DILUTION OF EXTERNAL CONTROLS FOR USE IN MICROARRAYS

CROSS-REFERENCE TO RELATED APPLICATIONS

This application claims the benefit of a U.S. Provisional Patent Application No. 60/619,008, filed Oct. 18, 2004, the entire disclosure of which is hereby expressly incorporated by reference.

BACKGROUND OF THE INVENTION

1. Field of the Invention

The present invention is related to the field of arrays more specifically to array systems.

2. Description of the Related Art

DNA arrays are commonly used to make quantitative or relative measurements of gene expression. They provide a medium for matching known and unknown DNA samples based on base-pairing rules and automating the process of identifying the unknowns. In general, arrays are described as macroarrays or microarrays, the difference being the size of the sample spots. Macroarrays contain sample spot sizes of about 300 microns or larger and can be easily imaged by existing gel and blot scanners. The sample spot sizes in microarrays are typically less than 200 microns in diameter and these arrays usually contain thousands of spots.

The microarrays contain nucleotide sequences corresponding to known genes or expressed sequence tags. A single microarray can contain thousands of genes, which may represent a significant subset of the genes, or even the entire genome, of an organism. A comparison of cells or tissues from experimental and control preparations provides data on differences in expression levels between the two conditions. For this purpose, mRNA is extracted from a sample, converted to complementary DNA (cDNA) and tagged with a fluorescent label. In a typical microarray experiment, cDNA from one sample (sample A) is labeled with a first dye that fluoresces in the red and cDNA from another sample (sample B) is labeled with a different dye that fluoresces in the green. The fluorescent red and green cDNA samples are then applied to a microarray that contains DNA fragments (oligonucleotides) corresponding to thousands of genes. If a DNA sequence probe is present on the microarray and its target complement is present in one or both samples, the sequences bind, and a fluorescent signal can be detected at the specific spot on the array. The signals are generally picked up using a "scanner" which creates a digital image of the array. The red to green fluorescence ratio in each spot reflects the relative expression of a given gene in the samples A and B.

Current microarray analyses rely on normalization and quality control methods that often assume evenly distributed changes, and/or absence of global shifts in gene expression across the array surface. Spotted microarray features such as housekeeping genes, sample pools, genomic DNA, or all genes on a microarray are typically used for normalization. Normalization based on these features is not always appropriate, especially for smaller focussed arrays (versus whole genome microarrays) where unbalanced changes are likely to occur, and will have significant effects on the relative hybridization signal intensities between biological samples. As a result, normalization based on such features will give rise to inaccurate interpretations of gene expression data.

According to WO2004/064482, normalization and quality assessment of microarray data, where unbalanced gene expression is anticipated, can be accomplished by the addition of several different external, non-species nucleic acid targets of different concentrations into the RNA sample of interest prior to labelling and hybridization. Different concentrations of external control targets are chosen to mimic a broad range of expression profiles. Probes complimentary to the external targets are printed at equivalent concentrations on the microarray. Variation between external control target concentrations in the sample results in different fluorescence intensities detected for each external control probe. Since detection of the different external controls will be equivalent between RNA samples, and are not affected by unbalanced or global shifts in gene expression within the RNA sample of interest, they can be used for accurate normalization and interpretation of gene expression data from focussed microarrays.

The drawback to using an external control, where varying amounts of different targets are added to the RNA sample of interest, is that it requires accurate measurement of extremely small quantities of those several RNA targets at low concentrations. The technical error associated with measurements at the low range required for microarray analysis results in unacceptable variation between samples that will have a significant influence on normalization and interpretation of gene expression data. In addition, the optimization and preparation of multiple external control targets and probes is time-consuming and costly.

Accordingly, there is a need for a microarray system that allows for more accuracy in the normalization of the data.

SUMMARY OF THE INVENTION

An object of the present invention is to provide a method that satisfies the above-mentioned need.

More particularly, the present invention provides a microarray and a hybridizing reagent that allow for more accuracy in the normalization of data.

The present invention teaches the addition of at least one external non-species nucleic acid or protein target, which can be accurately measured, to each biological sample prior to labelling and hybridization and the concurrent use of a matched external probe (either DNA, RNA or antibody) printed on the microarray in a series of different concentrations. The dilution of a control probe in situ (i.e. printed on the hybridization surface in different concentrations) effectively mimics a broad range of expression profiles. This approach allows an experimenter to apply at least one external control target spiked into RNA or protein samples reducing the preparation time a cost normally associated with the development and use of external controls.

Variation in the amount of printed probe will result in variation of the amount of hybridized external control target resulting in the detection of a broad range of hybridization signal intensities. Since the amount of external control target added to each biological sample is equivalent, and unaffected by unbalanced or global shifts in expression within the sample, detection of the external control will be equivalent across all samples. These external control features can then be utilized for normalization, quality control, validation or other applications.

The addition of a constant and an accurately measurable quantity of external control target to each biological sample prior to labelling and hybridization, combined with the printing of several different concentrations of the external control probe covering the dynamic range of signal detection, represents a novel approach to microarray normalization, quality control, validation and other applications that is unaffected by unbalanced or global shifts in gene expression.

The present invention presents the advantage of not relying on pipetting different concentrations and volumes of external DNA/RNA into reaction mixtures and is therefore much more accurate.

The present invention also has the advantage of providing means of carrying out in situ dilution in microarrays that are less expensive to operate and are not time consuming. In addition, the present invention presents the advantage of providing means of carrying out in situ dilution in microarrays used in toxicological studies or in comparing two states of a cell or in a study requiring the use of arrays or microarrays.

The present invention thus provides for an array system comprising:
- a solid support having at least one grid;
- at least one external control probe attached to at least one grid of the solid support in a series of concentrations, the concentrations are randomized in each grid;
- a hybridizing mixture containing at least one external control target complementary to the external control probe; and
- a plurality of sample probes attached to the solid support at discrete locations.

The present invention also provides a process of normalizing an array system, comprising the steps of:
a) providing a solid support comprising at least one grid;
b) attaching at least one external control probe to said solid support in a series of concentrations, each of said series of concentration of said at least one external control probe being attached to a grid of said solid support at a different discrete location from another concentration of said series, said series of concentrations being randomized in said grid;
c) attaching at least one sample probe on at least one grid to said solid support;
d) making several grids by repeating steps a) and b);
e) hybridizing the hybridizing mixture to the microarray;
f) measuring level of hybridization between the at least one external control probe and the at least one external control target and between the plurality of sample probes and plurality of sample targets; and
g) determining amount of sample target present in the hybridizing mixture.

The present invention also provides a kit comprising:
- a solid support having at least one grid;
- at least one external control probe attached to at least one grid of said solid support in a series of concentrations randomized in each grid;
- a hybridizing mixture containing at least one external control target complementary the external control probe; and
- a plurality of sample probes attached to the solid support at discrete locations.

Other objects and advantages of the present invention will be apparent upon reading the following non-restrictive detailed description, made with reference to the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

LIST OF TABLES

Figure 1:
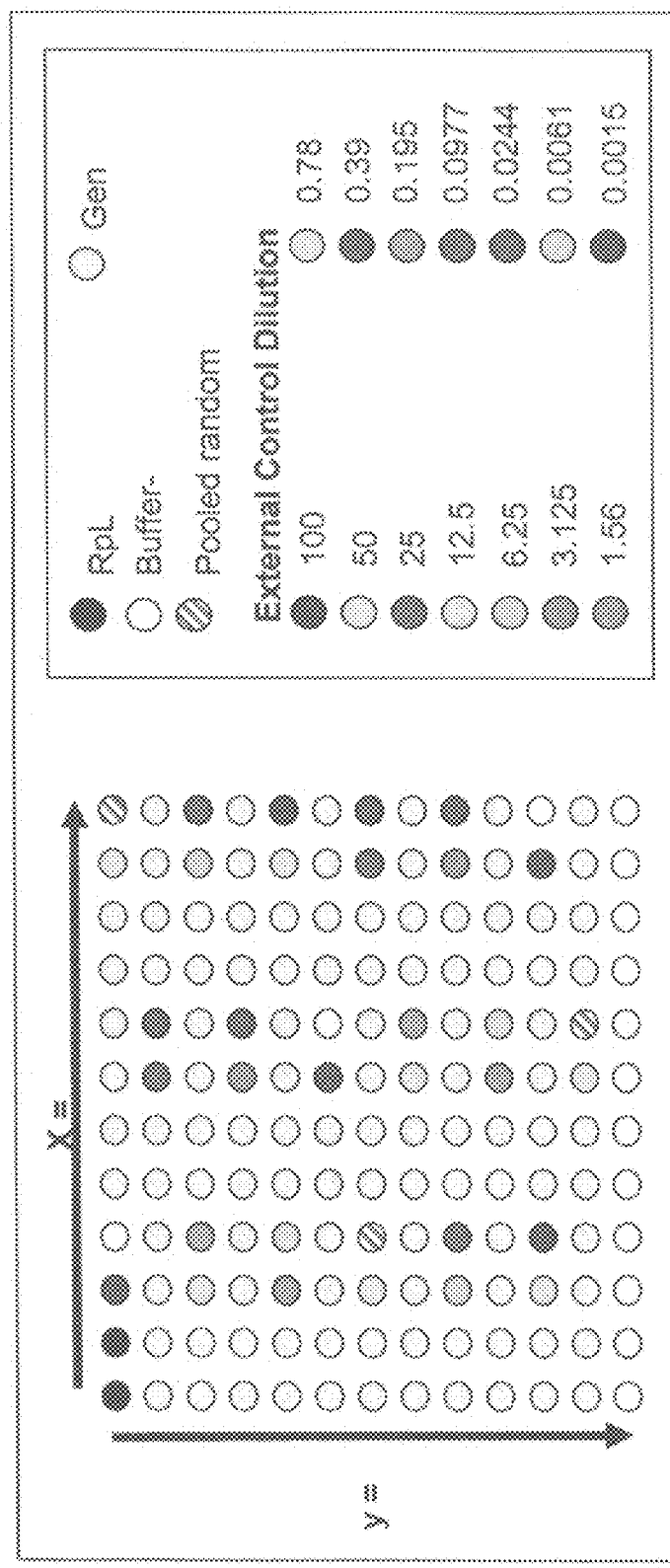
FIG. 1 shows a grid layout according to the invention.

Table 1 is a list of positive control house keeping genes.
Table 2 is a list of the commercial glass slides tested.
Table 3 is a list of the oligonucleotides printing buffers tested.

DETAILED DESCRIPTION OF THE PREFERRED EMBODIMENT

Definitions:

In order to provide an even clearer and more consistent understanding of the description, including the scope given herein to such terms, the following definitions are provided:

Gene refers to nucleic acid sequences (including both RNA or DNA) that encode genetic information for the synthesis of a whole RNA, a whole protein, or any portion of such whole RNA or whole protein.

Probe refers to a nucleotide sequence often an oligonucleotide that is, or is intended to be, attached to a solid support in an array that can be used to hybridize with and thereby identify the presence of a complementary sequence, or a complementary sequence differing from the probe sequence but not to a degree that prevents hybridization under the hybridization stringency conditions used. As is well known to those skilled in the art, for the hybridization characteristics to be similar across a wide range of oligonucleotides, it is typically required that the probes on the array be of the substantially same length, have a similar percentage of Guanine to Cytosine content and lack any extensive runs of poly A, poly G, poly C, or poly T tracts. The goal of controlling these parameters is to produce probes that have similar melting and hybridization temperatures. Additionally, these probes should, preferably, lack length complementary regions and not form hairpin structures. The probe can be DNA, RNA, oligonucleotides, cDNA, proteins or antibodies.

Target refers to nucleic acids intended to be hybridized (or bound) to probes immobilized on microarrays by sequence complementarity. The target can be DNA, RNA, oligonucleotides, cDNA, proteins or antibodies. As is well-known in the art, target nucleic acids may be obtained from a wide variety of organisms (bacteria, plants . . . ), tissues or cells. Methods and techniques for the extraction, manipulation and preparation of nucleic acids for hybridization reactions are well-known in the art (see, for example, J. Sambrook et al., "Molecular Cloning: A Laboratory Manual", 1989, 2nd Ed., Cold Spring Harbor Laboratory Press: New York, N.Y.; "PCR Protocols: A Guide to Methods and Applications", 1990, M. A. Innis (Ed.), Academic Press: New York, N.Y.; P. Tijssen "Hybridization with Nucleic Acid Probes-Laboratory Techniques in Biochemistry and Molecular Biology (Parts I and II)", 1993, Elsevier Science; "PCR Strategies", 1995, M. A. Munis (Ed.), Academic Press: New York, N.Y.; and "67 Protocols in Molecular Biology", 2002, F. M. Ausubel (Ed.), 5th Ed., John Wiley & Sons).

Complement when used in reference to a given polynucleotide sequence refers to a sequence of nucleotides which can form a double-stranded heteroduplex in which every nucleotide in the sequence of nucleotides is base-paired by hydrogen bonding to a nucleotide opposite it in the heteroduplex with the given polynucleotide sequence. The term may refer to a DNA or an RNA sequence that is the complement of another RNA or DNA sequence. As used herein, the term "hybridizes" refers to the formation of a hydrogen-bonded heteroduplex between two nucleic acid molecules. Generally, a given nucleic acid molecule will hybridize with its complement, or with a molecule that is sufficiently complementary to the given molecule to permit formation of a hydrogen-bonded heteroduplex between the two molecules.

Oligonucleotide Oligonucleotides means nucleic acid, either desoxyribonucleic acid (DNA), or ribonucleic acid (RNA), in single-stranded or double-stranded form and having one nucleotide or more whether, occurring naturally or non-naturally in a particular cell, tissue or organism, and any chemical modifications thereof. Such modifications include, but are not limited to providing other chemical groups that incorporate additional charge, polarizability, hydrogen bonding or electrostatic interaction to one or more of nucleic acid bases of the oligonucleotide.

Specifically hybridizing refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

Toxicant refers to any substance potentially toxic. It also refers a chemical having the qualities or effects of a poison and to a harmful substance or agent that may injure an exposed organism. Toxicants according to the present invention may be chemical toxicants like for instance cyanides, phenols, pesticides, or heavy metals. Toxicants may also be physical in nature like for instance asbestos, silicas and they may also be radioactive.

Normalization refers to the process of removing superfluous differences in array or microarray data by reducing them to a common denominator.

External refers to a molecule that does not hybridize with the molecules of the collection or sample under study. In a preferred embodiment, a nucleic acid sequence is thus "external" if its complement is not present in the nucleic acids of a collection. The source or collection may preferably be a plurality of nucleic acids to be hybridized to an array. The external control probe has a sequence that does not hybridize to a target from the plurality of targets from an organism under study to be hybridized on an array or microarray.

Hybridizing mixture refers to a mixture being or intended to be hybridized to an array. Those of ordinary skill in the art will appreciate that the hybridizing sample may contain DNA, RNA, or both, but most commonly contains cDNA. The hybridizing mixture typically contains nucleic acids whose hybridization with probes on an array is detectable. For example, in many embodiments, the hybridizing mixture comprises or consists of detectably labelled nucleic acids.

Labelled, Detectably labelled, labelled with a detectable agent: specify that a nucleic acid molecule or individual nucleic acid segments from a sample can be detected and/or visualized following binding (i.e. hybridization) to probes immobilized on an array. The detectable agent is such that it generates a signal which can be measured and whose intensity is related to the amount of hybridized nucleic acids. The detectable agent is such that it generates a localized signal, thereby allowing spatial resolution of the signal from each spot on the array. Methods for labelling nucleic acid molecules are well known in the art. Suitable detectable agents include, but are not limited to: various ligands, radionuclides, fluorescent dyes, chemiluminescent agents, microparticles, enzymes, calorimetric labels, magnetic labels, and haptens.

Fluorescent label refers to a molecule, which, in solution and upon excitation with light of appropriate wavelength, emits light back. Numerous fluorescent dyes of a wide variety of structures and characteristics are suitable for use in the practice of this invention. Similarly, methods and materials are known in the art for fluorescently labelling nucleic acids (see, for example, R. P. Haugland, "Molecular Probes: Handbook of Fluorescent Probes and Research Chemicals 1992-1994", Sti' Ed., 1994, Molecular Probes, Inc.). In choosing a fluorophore, it is generally preferred that the fluorescent molecule absorbs light and emits fluorescence with high efficiency (i.e., it has a high molar absorption coefficient and a high fluorescence quantum yield, respectively), and is photostable (i.e. it does not undergo significant degradation upon light excitation within the time necessary to perform the array-based hybridization). Suitable fluorescent labels for use in the practice of the methods of the invention include, for example, Cy-3, Cy-5, Texas red, FITC, Spectrum Red, Spectrum Green, Alexa-488, phycoerythrin, rhodamine, fluorescein, fluorescein isothiocyanine, carbocyanine, merocyanine, styryl dye, oxonol dye, BODIPY dye, and equivalents, analogues or derivatives of these molecules.

Array refers to an arrangement on a solid support of multiple nucleic acid molecules of known or unknown sequences. These nucleic acid molecules are attached to discrete "spots" or positions on the support. A discrete spot may contain a single nucleic acid molecule or a mixture of different nucleic acid molecules. Spots on an array may be arranged on the support surface at different densities. In general, microarrays with probe pitch smaller than 500 pm (i.e., density larger than 400 probes per cm²) are referred to as high density microarrays, otherwise, they are called low density microarrays. Arrays come as two-dimensional probe matrices (or supports), which can be solid or porous, planar or non-planar, unitary or distributed. The term "microarray" more specifically refers to an array that is miniaturized so as to require microscopic examination for visual evaluation. Arrays used in the invention are preferably microarrays.

Expression refers to the process by which nucleic acid is transcribed into mRNA and translated into peptides, polypeptides, or proteins.

Nucleic acid refers to either desoxyribonucleic acid (DNA), or ribonucleic acid (RNA).

Polynucleotide refers to any DNA, RNA sequence or molecule having one nucleotide or more, including nucleotide sequences encoding a complete gene. The term is intended to encompass all nucleic acids whether occurring naturally or non-naturally in a particular cell, tissue or organism. This includes DNA and fragments thereof, RNA and fragments thereof, cDNAs and fragments thereof, expressed sequence tags, artificial sequences including randomized artificial sequences.

Kit may comprise packages, each containing one or more of the various reagents (typically in concentrated form) required to perform the respective tests. The kits according to these embodiments of the invention are contemplated to be useful for detecting and/or quantifying DNA, RNA, and/or protein in biological (or other types of) samples.

General Overview of the Invention

The present inventors have discovered that it is possible to normalize microarrays by using external control probes in a series of dilutions across the microarray itself. Therefore the present invention is directed towards an array or a microarray having a series of dilutions of an external probe attached to it, a process of normalization by using such a series of concentrations of an external probe and also a kit comprising the array containing the series of concentrations of the external probe and a hybridizing buffer containing the external control target.

Other objects and advantages of the present invention will be apparent upon reading the following non-restrictive description of several preferred embodiments and the accompanying examples.

Description of Preferred Embodiments

The inventors have found a way to normalize an array or a microarray by using a series of concentrations of an external control probe spanning all areas of a grid in the array or microarray. Thus the present invention provides for an array system comprising:
  a solid support having at least one grid;
  at least one external control probe attached to the grid in a series of concentrations which is randomized in the grid;
  a hybridizing mixture containing at least one external control target complementary to the external control probe; and
  a plurality of sample probes attached to the solid support at discrete locations.

According to a preferred embodiment of the invention, the array system is a microarray system.

In a preferred embodiment, the sample probes and the external control probes are printed on the solid support. In a more preferred embodiment the printing is done by a CHIPWRITEPRO® (BioRad). According to another preferred embodiment of the invention, the CHIPWRITEPRO® has 12 pins, and as can be seen in FIG. 1, each pin produces a distinct grid with x rows and y columns. The external control probe is a molecule that does not hybridize with the molecules of the collection or sample under study. This in situ approach of printing of the series of concentrations of the external control probe, does not rely on pipetting different concentrations and volumes of different RNA/DNA into reaction mixture and is therefore much more accurate.

The array system according to the invention is further characterized by a hybridizing mixture, which comprises a plurality of sample targets to be hybridized on the array. According to a preferred embodiment of the invention, the external control probe and the sample probes of the array are chosen from DNA, RNA, oligonucleotides, cDNA, proteins and antibodies and more preferably they are oligonucleotides, and even more preferably 70mer oligonucleotides. The external control probe may be from a bacterial, plant, animal gene or from any other organism. In a preferred embodiment of the invention, the external control probe is an oligo probe designed for the *Arabidopsis thaliana* chlorophyll synthase gene and the external control target is RNA prepared through in vitro transcription of *A. thaliana* chlorophyll synthase cDNA.

The concentration of the external control probe is chosen to start at extremely low molarity and going up to saturation. These concentrations are chosen to mimic the range of the expression profile of the studied sample and allow the control for differential hybridization occurring across the chip. In a preferred embodiment of the invention, the series of concentrations of the external control probe varies from 0.0015 to 100 μM. In a more preferred embodiment of the invention, the series of concentrations of the external control probe is 0.0015, 0.0031, 0.0061, 0.0122, 0.0244, 0.0977, 0.0077, 0.195, 0.39, 0.78, 1.5625, 3.125, 6.25, 12.5, 25, 50, 60, 80 and 100 μM. As can be appreciated from FIGS. 2A and 2B, showing preferred embodiments of the invention, the series of concentrations is spatially randomized and duplicated on a grid. A grid also contains at least one spot with buffer, spots that are left empty and at least one spot printed with a housekeeping gene, the house keeping gene probe being preferably RpL5.

As mentioned above, the sample probes are chosen from DNA, RNA, oligonucleotides, cDNA, proteins and antibodies. These samples probes are representative of relevant genes under study. In a preferred embodiment, the relevant genes under study are toxicologically relevant genes. According to a preferred embodiment, the sample probes are oligonucleotides. In another preferred embodiment of the invention the sample probes oligonucleotides are 70mer oligonucleotides. In yet another preferred embodiment of the invention, the 70mer oligonucleotides are designed and synthesized according to the following characteristics:
  less than 60% G C content
  less than 1000 basis from the 3' end;
  longest stem being less than 9 bases;
  less than 20% cross homology; and/or
  less than 20 contiguous bases in common with top BLAST hit gene.
  The invention is further characterized in that the sample probes are attached to the solid support in a fixed concentration. Hence, the 70mer oligonucleotides of the invention are attached to the solid support in a fixed concentration. In a preferred embodiment of the invention, the 70mer oligonucleotides are attached to the solid support at a concentration chosen from 60, 40, 30, 15, 7.5 and 3.5 μM and preferably at the concentration of 40

μM. In a preferred embodiment of the invention, the 70mer oligonucleotides are representative of toxicologically relevant genes in regulatory toxicology and risk assessment studies.

As can be appreciated in FIG. 1, according to a preferred embodiment of the invention, the array system is further characterized in that the series of concentrations is spatially randomized across a grid and attached in duplicate in each grid of the array. Having at least two copies of different dilutions of the external control spanning the area across a chip, allows the control of differential hybridization. As can be appreciated also from FIG. 1:

The array system is further characterized in that the series of concentrations of the external control probe varies from 0.0015 to 100 μM. More preferably the series of concentrations of the at least one external control probe is 0.0015, 0.0031, 0.0061, 0.0122, 0.0244, 0.0977, 0.0077, 0.195, 0.39, 0.78, 1.5625, 3.125, 6.25, 12.5, 25, 50, 60, 80 and 100 μM.

The invention also provides for the process of normalizing an array system, comprising the steps of:
  a) providing a solid support comprising at least one grid;
  b) attaching at least one external control probe to the solid support in a series of concentrations, each concentration of the series is attached to a grid of the array at a different discrete location, the concentrations are also randomized in the grid;
  c) attaching sample probes spatially arranged in the grid;
  d) making several grids on the solid support by repeating steps a) and b);
  e) hybridizing the hybridizing mixture to the microarray;
  f) measuring level of hybridization between the at least one external control probe and the at least one external control target and between the plurality of sample probes and plurality of sample targets; and
  g) determining amount of sample target present in the hybridizing mixture.

In a preferred embodiment of the invention the series of concentration of the external control probe of the process varies from 0.0015 to 100 μM and even more preferably it is 0.0015, 0.0031, 0.0061, 0.0122, 0.0244, 0.0997, 0.0077, 0.195, 0.39, 0.78, 1.5625, 3.125, 6.25, 12.5, 25, 50, 60, 80 and 100 μM.

In another preferred embodiment of the invention the sample probes and the external control probes are from DNA, RNA, oligonucleotides, cDNA, proteins and antibodies, more preferably oligonucleotides. In a preferred embodiment of the invention the sample probes of the process are 70mer oligonucleotides, more preferably designed and according to the following characteristics:
  less than 60% G C content
  less than 1000 basis from the 3' end;
  longest stem being less than 9 bases;
  less than 20% cross homology; and/or
  less than 20 contiguous bases in common with top BLAST hit gene.

According to a preferred embodiment of the invention, the process is further characterized in that it comprises the following step:
  h) attaching the at least one external control probe series of concentration in duplicate in the grid.

In another preferred embodiment of the invention, the process is further characterized in that it comprises at least one of the following steps:
  i) adding a buffer only to at least one discrete spot on the grid;
  j) leaving at least one discrete spot in said grid empty;
  k) attaching a random hexamer to one spot on said grid;
  l) attaching a random pool of 70mer oligonucleotides to at least one discrete spot on said grid; and
  m) attaching a probe from a housekeeping gene to at least one discrete spot on said grid.

In a preferred embodiment of the invention, the 70mer oligonucleotides are attached to the solid support at a concentration chosen from 60, 40, 30, 15, 7.5 and 3.5 μM and more preferably at 40 μM.

The composition and the method of preparation of the buffer of step e) is well known in the art. In a preferred embodiment of the present invention, the buffer is PBS®, QUANTIFOIL I®, QUANTIFOIL II® and ARRAYIT®, and more preferably ARRAYIT®. In a preferred embodiment of the invention, the housekeeping gene is RpL5.

In a preferred embodiment of the invention, and as can be seen from FIGS. 2A, 2B, and 2C, the buffer can be added to one spot, 6 or 7 spots in the grid. Also in a preferred embodiment of the invention, no spot or one or 4 spots of the grid are left empty. In a preferred embodiment, the house keeping gene is RpL5. Also in a preferred embodiment of the invention, the housekeeping gene probe is attached to one, 3 or 4 spots in the grid, and a random pool of 70mer oligonucleotides is attached to 3 spots in the grid. The series of concentrations of external control probe is also duplicated across the grid spanning all its area. In a more preferred embodiment, the housekeeping gene is RpL5.

The process of the invention is even further characterized in that it comprises the step of:
  n) attaching a plurality of sample probes in other discrete spots of each said grid as can also be appreciated from FIGS. 2A, 2B and 2C.

The process of the invention is further characterized by that the hybridization mixture comprises a plurality of sample targets to be hybridized on the array. The hybridization, the measurement of the level of hybridization and the determination of the amount of sample target present in the hybridizing mixture are done according to methods well known by a person in the art.

Figure 2:
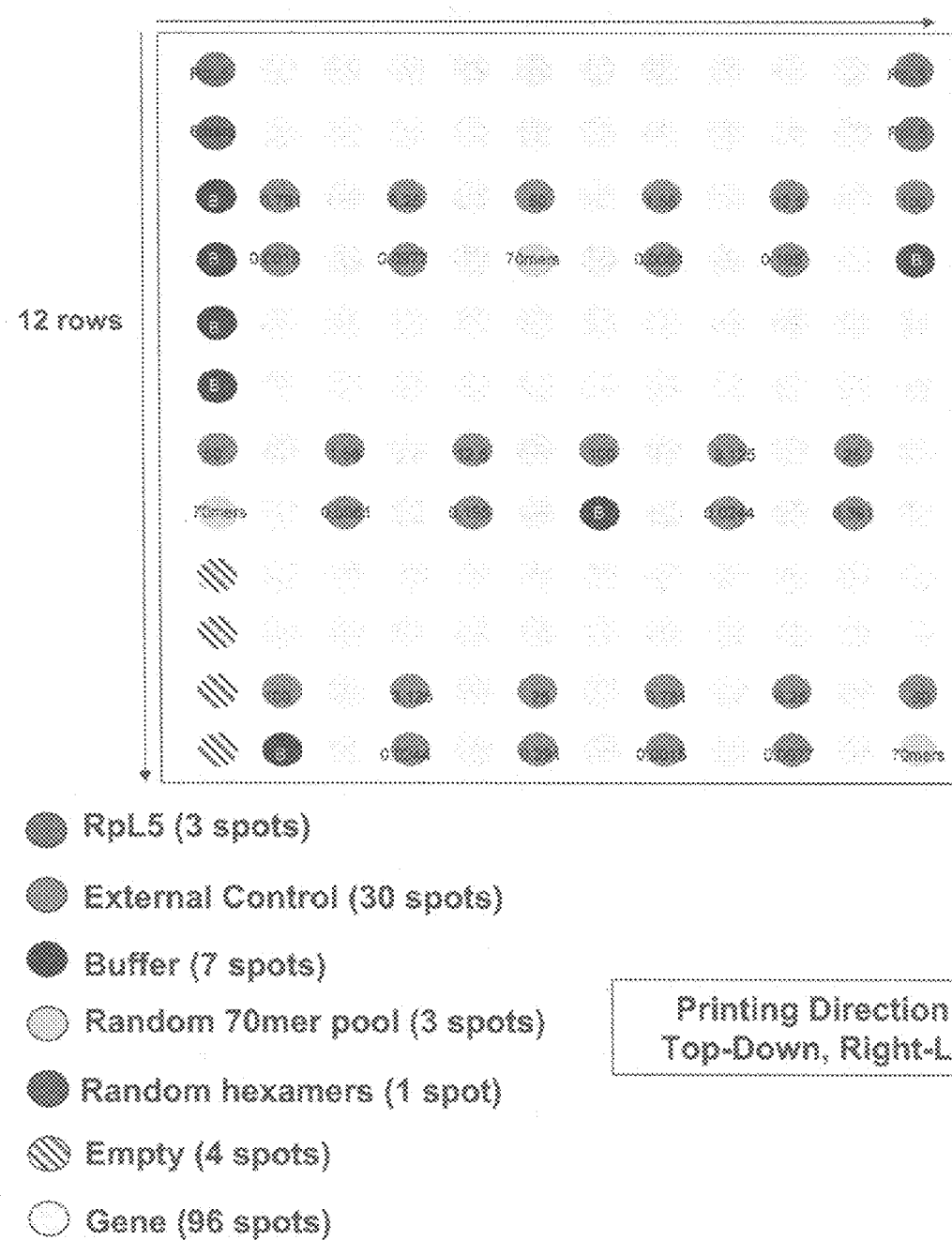
FIGS. 2A, B and C show other grid layouts according to the invention.
Figure 2:
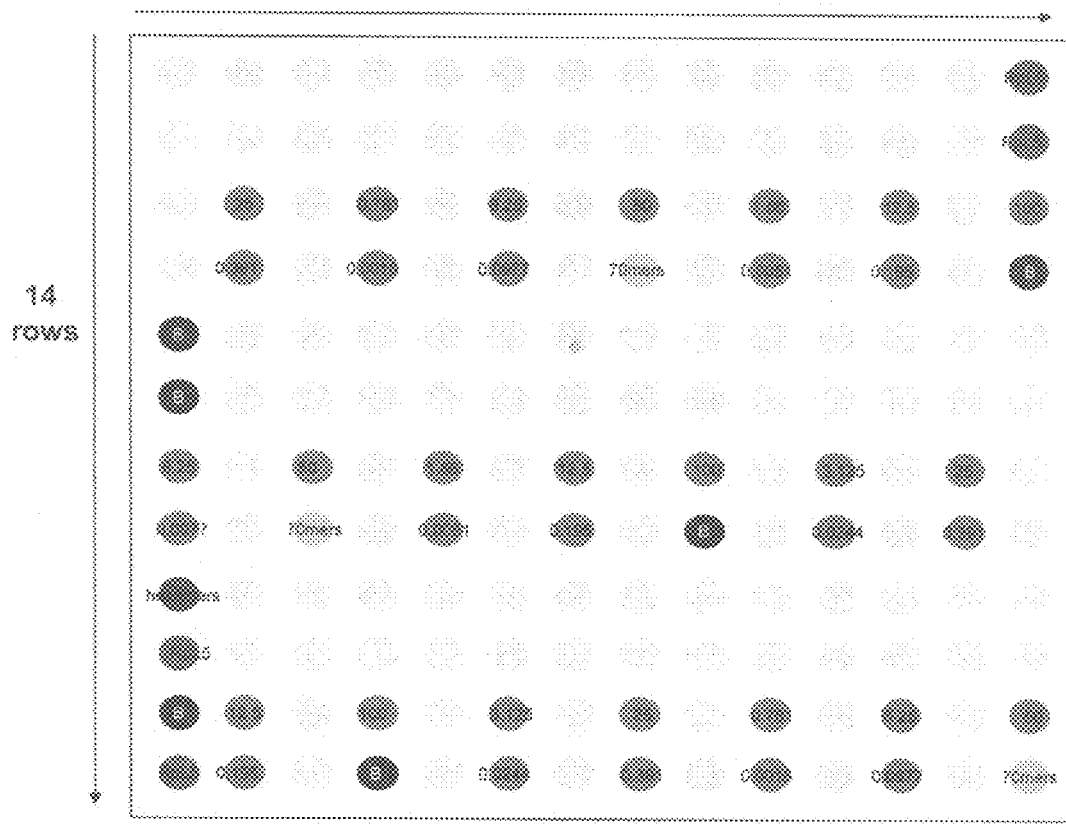
Figure 2:
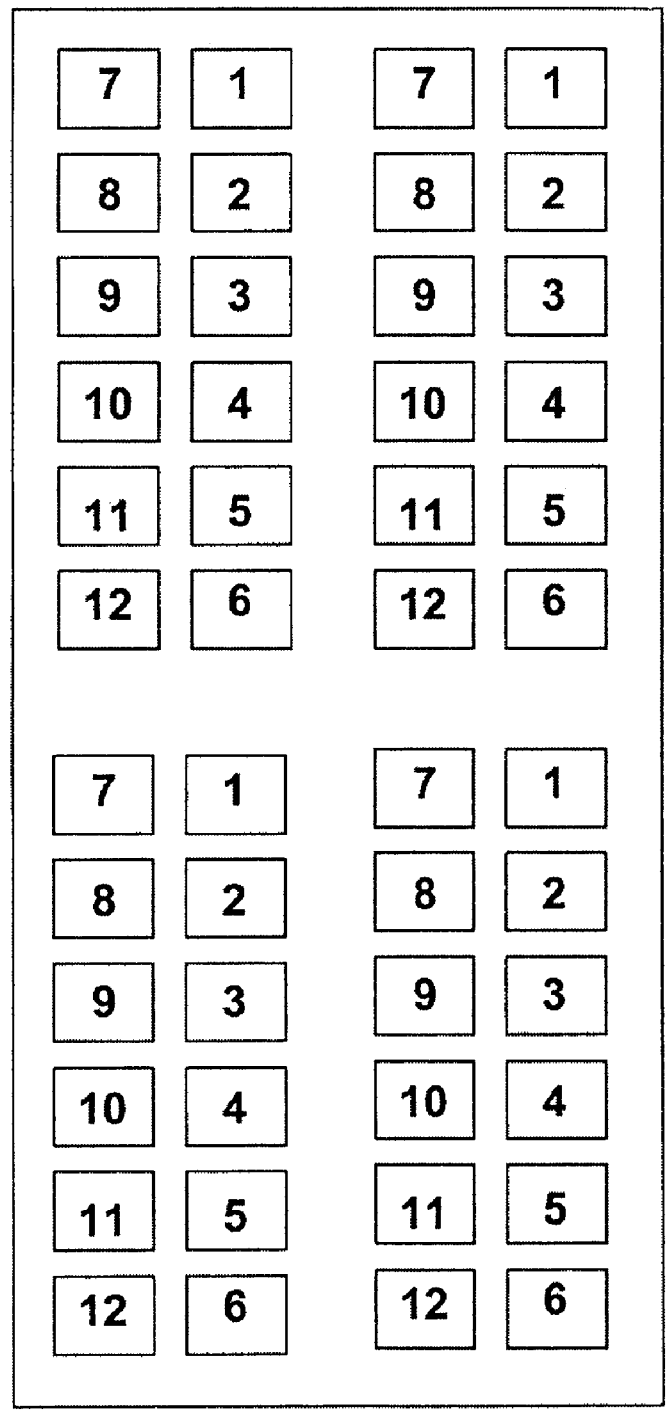
Figure 3:
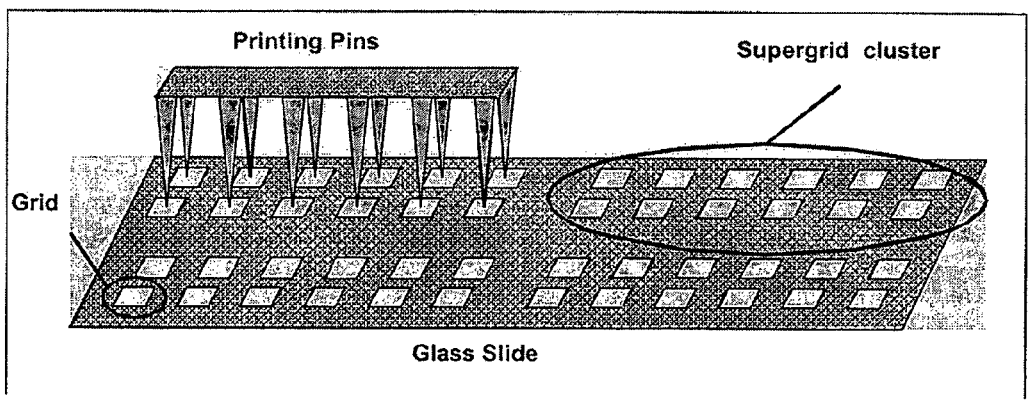
FIG. 3 shows a diagrammatic representation of microarray printing with VIRTEK CHIPWRITEPRO® (BioRad) using 12 pins.

According to a preferred embodiment of the invention, and as can be seen in FIG. 3, the external control probe and the sample probes are printed on the solid support, and more preferably by a VIRTEK CHIPWRITEPRO® (BioRad). According to another preferred embodiment of the invention, the VIRTEK CHIPWRITEPRO® has 12 pins, and as can be seen in FIG. 1, each pin produces a distinct grid with x rows and y columns. In a preferred embodiment of the invention, each grid can be 12 ×12, 12 ×13 or 12 ×14. The 12 distinct grids printed by each pin represent a supergrid cluster. The supergrid cluster is then replicated across the surface of the glass slide to produce the final microarray. In a preferred embodiment of the invention, the supergrid is replicated 4 times as can be appreciated in FIGS. 1 and 2C.

The present invention also provides for a kit comprising:
  a solid support having at least one grid;
  at least one external control probe, said at least one external control probe being attached to at least one grid of said solid support in a series of concentrations, said series of concentrations being randomized in said at least one grid;
  a hybridizing mixture containing at least one external control target being complementary to said at least one external control probe; and
  a plurality of sample probes attached to said solid support at discrete locations.

The kit is further characterized in that the hybridizing mixture further comprises a plurality of sample targets to be hybridized on the array.

In a preferred embodiment of the invention the series of concentrations of the external control probe of the kit varies from 0.0015 to 100 μM. and more preferably it is 0.0015, 0.0031, 0.0061, 0.0122, 0.0244, 0.0977, 0.0077, 0.195, 0.39, 0.78, 1.5625, 3.125, 6.25, 12.5, 25, 50, 60, 80 and 100 μM.

In a preferred embodiment of the invention the external control probe and the sample probes of the kit of the invention are chosen from DNA, RNA, oligonucleotides, cDNA, proteins and antibodies and more preferably the external control probe and the sample probes of the kit are oligonucleotides, the oligonucleotides are even more preferably 70mer oligonucleotides. In a preferred embodiment of the invention 70mer oligonucleotides of the kit are designed and synthesized according to the following characteristics:

less than 60% G C content
less than 1000 basis from the 3' end;
longest stem being less than 9 bases;
less than 20% cross homology; and/or
less than 20 contiguous bases in common with top BLAST hit gene.

In another preferred embodiment of the invention the 70mer oligonucleotides of the kit are attached to the solid support at a concentration chosen from 60, 40, 30, 15, 7.5 and 3.5 μM and more preferably at 40 μM.

EXAMPLES

The following examples are illustrative of the applicability of the present invention and are not intended to limit its scope. Modifications and variations can be made therein without departing from the spirit and scope of the invention. Although any method and material similar or equivalent to those described herein can be used in the practice for testing of the present invention, the preferred methods and materials are described. The following experimental procedures and materials were used for the examples set fort below in the normalization of the inventors TOXARRAY®.

A. Materials and Methods

1. Gene Selection and Probe Design

Genes predictive of toxicant exposure were established from in house gene expression data, gene expression studies in the current literature, and statistical re-analysis of publicly available microarray data.

Figure 4:
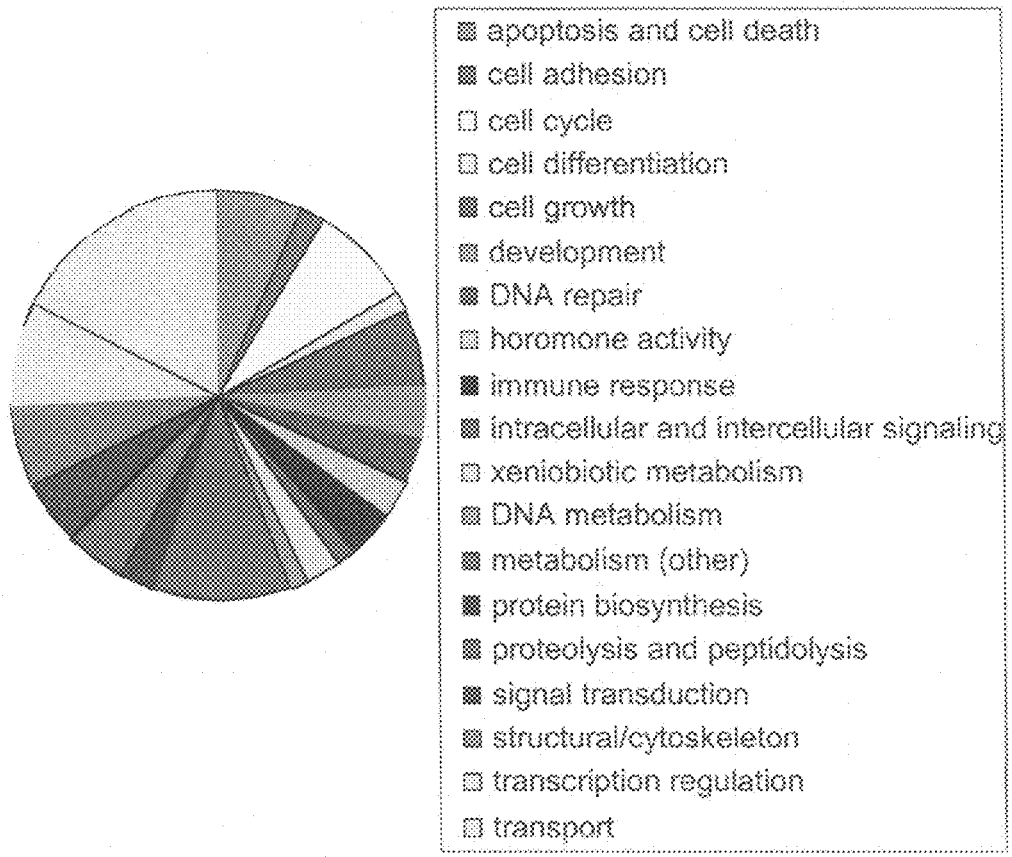
FIG. 4 shows the TOXARRAY® genes sorted by ontology.

The following information was acquired through publicly available databases for each gene:
Official gene symbol and name
Gene sequence (RefSeq or GenBank accession number)
UniGene Cluster ID
Alternate gene names and aliases
Ontology
LocusLink ID
Ensemble Gene ID
Ensembl Transcript ID The current list consists of ~1100 genes. FIG. 4 displays the gene list grouped by ontology.

Custom 70mer oligonucleotides were designed and synthesized for each gene by Qiagen according to the following criteria:

less than 60% GC content
less than 1000 bases from the 3' end
Longest stem less than 9 bases
less than 70% cross homology
less than 20 contiguous bases in common with top BLAST hit gene.

2. Oligonucleotide Test Set

Prior to printing the high density array, a set of control oligos provided by Qiagen were used to optimize array printing and hybridization protocols. These comprise:

Positive control oligos designed for common housekeeping genes (Table 1).
Random 70mer oligos designed to have no cross homology to any known mouse genes.

TABLE 1

| Gene Symbol | Gene Name |
|---|---|
| Ldh1 | Lactate dehydrogenase 1, A chain |
| Hsp70-3 | Heat shock protein, 70 kDa 3 |
| Gapd | Glyceraldehyde-3-phosphate dehydrogenase |
| Ubb | Ubiquitin B |
| Tcea1 | Transcription elongation factor A (SII) 1 |
| Eif4a2 | Eukaryotic translation initiation factor 4A2 |
| Cyc1 | Cytochrome c-1 |
| Tcfe2a | Transcription factor E2a |
| Nup62 | Nucleoporin 62 |
| Rpl5 | Ribosomal protein L5 |
| Top1 | Topoisomerase (DNA) I |
| Hsp84-1 | Heat shock protein, 84 kDa 1 |

In addition to the test oligos provided by Qiagen, buffer-only and random hexamers were also printed on our initial microarrays as negative control features.

3. In House Microarray Printing

Microarray printing was performed by the VIRTEK CHIP-WRITEPRO® (BioRad). An example of printing a microarray using 12 printing pins is represented in FIG. 3.

4. Target Labeling and Hybridization Protocols

Universal mouse reference RNA (Stratagene) was used for all target labelling and array hybridizations. All array experiments were carried out in two colours, Cy5 and Cy3, using the cRNA linear amplification and fluorescent labelling kit from Agilent Technologies. All arrays were processed in an automated hybridization station (Tecan), images were obtained with SCANARRAY EXPRESS® confocal laser scanner (Packard BioSystems), and image analysis was performed by QUANTARRAY® image analysis software (Packard Biosystems).

B. Results

1. Glass Slide and Oligo Printing Buffer Selection

Figure 5:
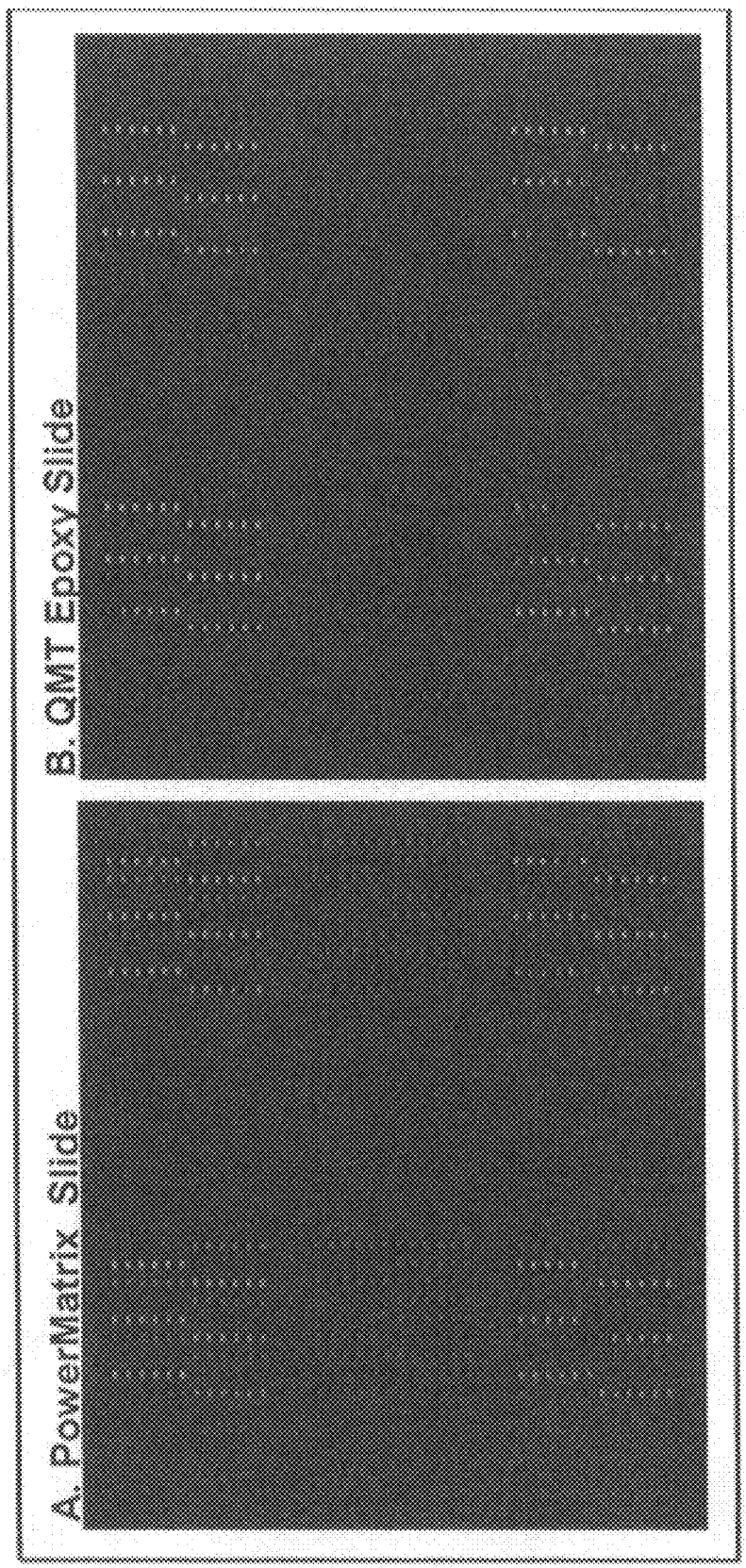
FIG. 5 is images of identical hybridizations of oligo test set on two slide types showing (arrows) the increase in detectable test oligo spots on the POWERMATRIX® slide (a) compared to the QMT EPOXY® slide (b).

The POWERMATRIX® and QMT EPOXY® slides produced significantly lower background signals compared to all other slides tested (data not shown). The POWERMATRIX® slide was chosen over the QMT EPOXY® slide because of its ability to detect more of the test oligo spots (FIG. 5).

Figure 6:
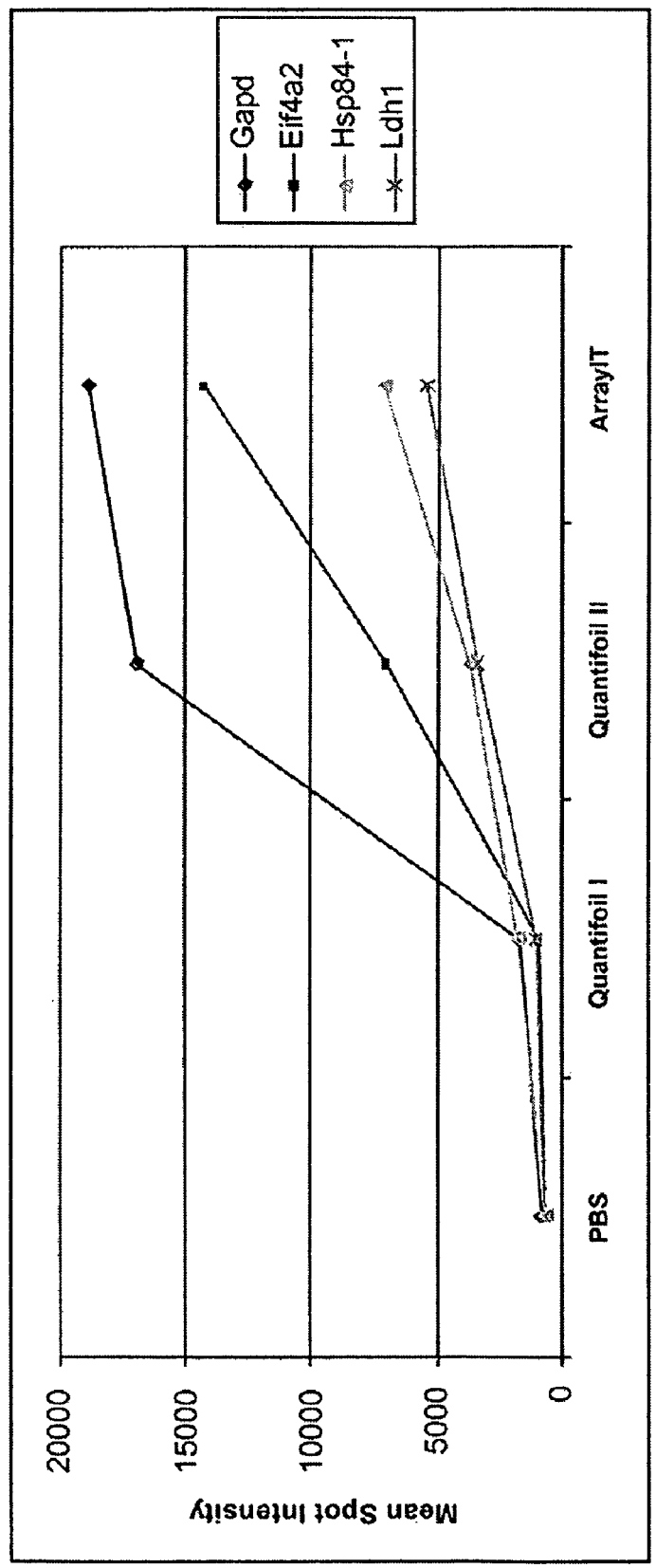
FIG. 6 shows the effect of oligo spotting buffer on mean spot intensity.
Figure 7:
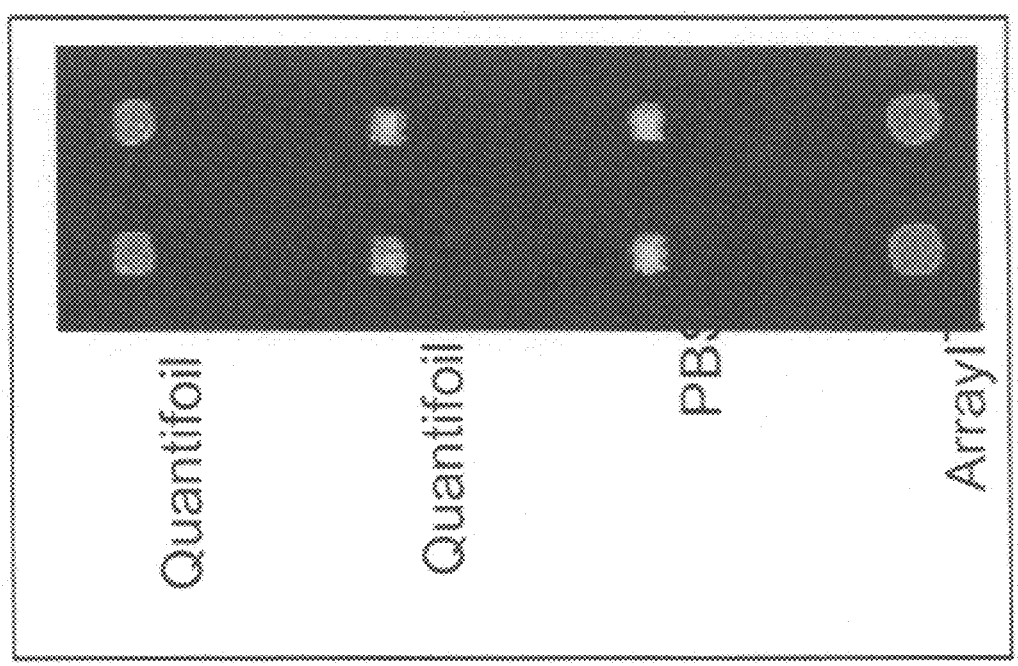
FIG. 7 shows a partial microarray image of Hsp84-1 oligo printed in 4 different printing buffers on the POWERMATRIX® slide.

Oligo spotting buffer had a significant effect on spot intensity:

ARRAYIT® spotting solution produced spots with the highest signal intensities while PBS and QUANTIFOIL I® spotting solutions produced spots with the lowest signal intensities (FIG. 6). ARRAYIT® also produces the best quality spots based on spot size and morphology (FIG. 7).

Tables 2 and 3 list respectively the glass slides and the oligo printing buffers tested.

TABLE 2

| Slide Name | Manufacturer |
|---|---|
| QMT Epoxy | Quantifoil Micro Tools GmbH |
| PowerMatrix | Full Moon Biosystems |
| SuperChip epoxysilane | Erie Scientific |
| SuperAldehyde | Telechem International |
| CodeLink Activated | Amersham Biosciences |
| SpotOn | Scandinavian Micro Biodevices |

TABLE 3

| Oligo Printing Buffer | Manufacturer |
|---|---|
| ArrayIT | Telechem International |
| Spotting Solution I | Quantifoil Micro Tools GmbH |
| Spotting Solution II | Quantifoil Micro Tools GmbH |
| Phosphate Buffered Saline (PBS) | In house |

2. Optimization of Oligo Printing Concentration

To determine the optimal printing concentration, the oligo test set was printed at 60, 40, 30, 15, 7.5, and 3.75 µM.

Figure 8:
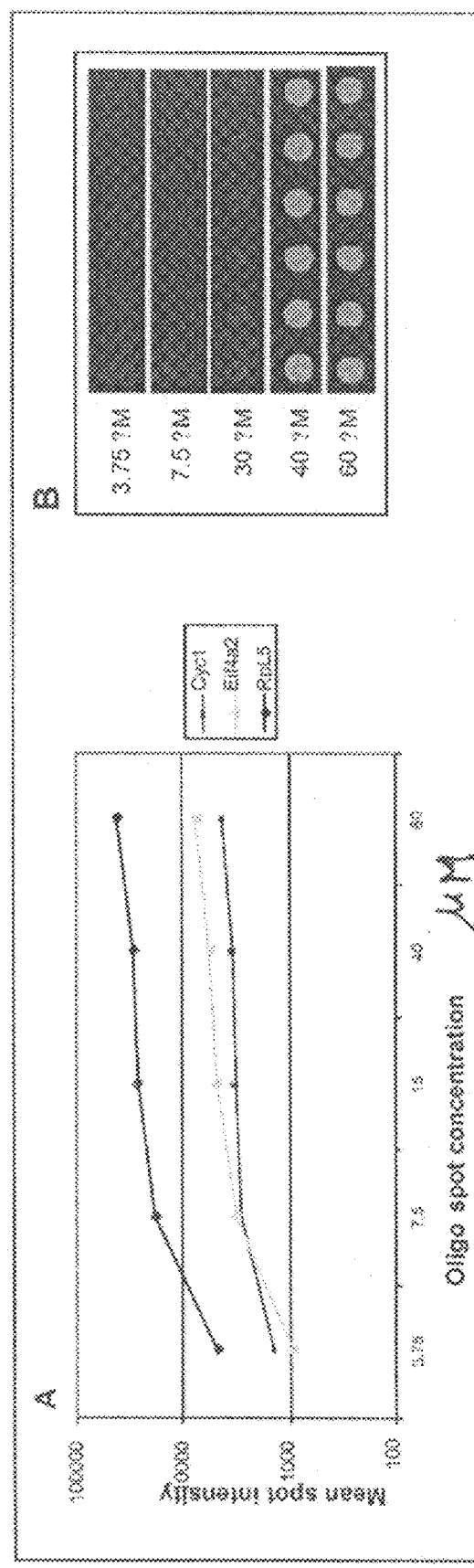
FIG. 8 shows the effect of oligo printing concentration on signal intensities. A is the logarithmic plot of mean spot intensities of a subset of test oligos printed at different concentrations. B is the image of a subset of RpL5 oligo printing concentration.

Large intensity gains are apparent when the oligo printing concentration is increased to 40 µM (FIG. 8).

Intensity gains were minimal for printing concentrations >40 µM (FIG. 8).

Figure 9:
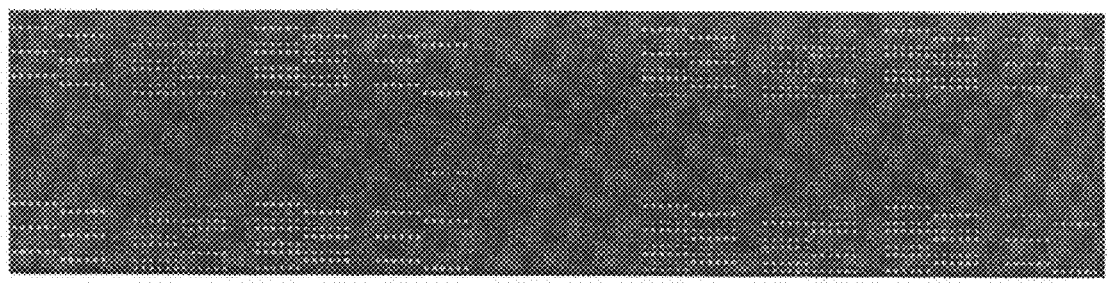
FIG. 9 shows a typical microarray image of oligos test set printed at 40 µM, in ARRAYIT® spotting solution (Telechem International) on the POWERMATRIX® slide (Full Moon Biosystems).

The optimal oligo printing concentration was determined to be 40 µM, FIG. 9 displays a typical microarray image of the oligo test set printed under optimal oligo printing concentration, printing buffer, and glass slide.

3. Microarray Normalization Feature

The majority of microarray analyses rely on normalization methods that assume evenly distributed changes and/or absence of global shifts using microarray features such as housekeeping genes, spotted microarray sample pools, genomic DNA, or all genes.

Normalization based on the above features are not appropriate for the inventors TOXARRAY® because global unbalanced changes are expected due to its relatively small size and the fact that genes were chosen based on evidence of transcript level changes as a result of toxicant exposure.

The use of external control features, made up of a non-murine oligonucleotide and specific RNA, allows a better comparison between slides and overcomes the problem of global changes in gene expression.

In addition to their use in normalization, external control features can also be used to cope with local, intensity-dependent systematic variation by representation in sufficient numbers in each grid and to monitor sample labelling and optimization of microarray hybridization protocols.

4. External Control Feature Design

Figure 10:
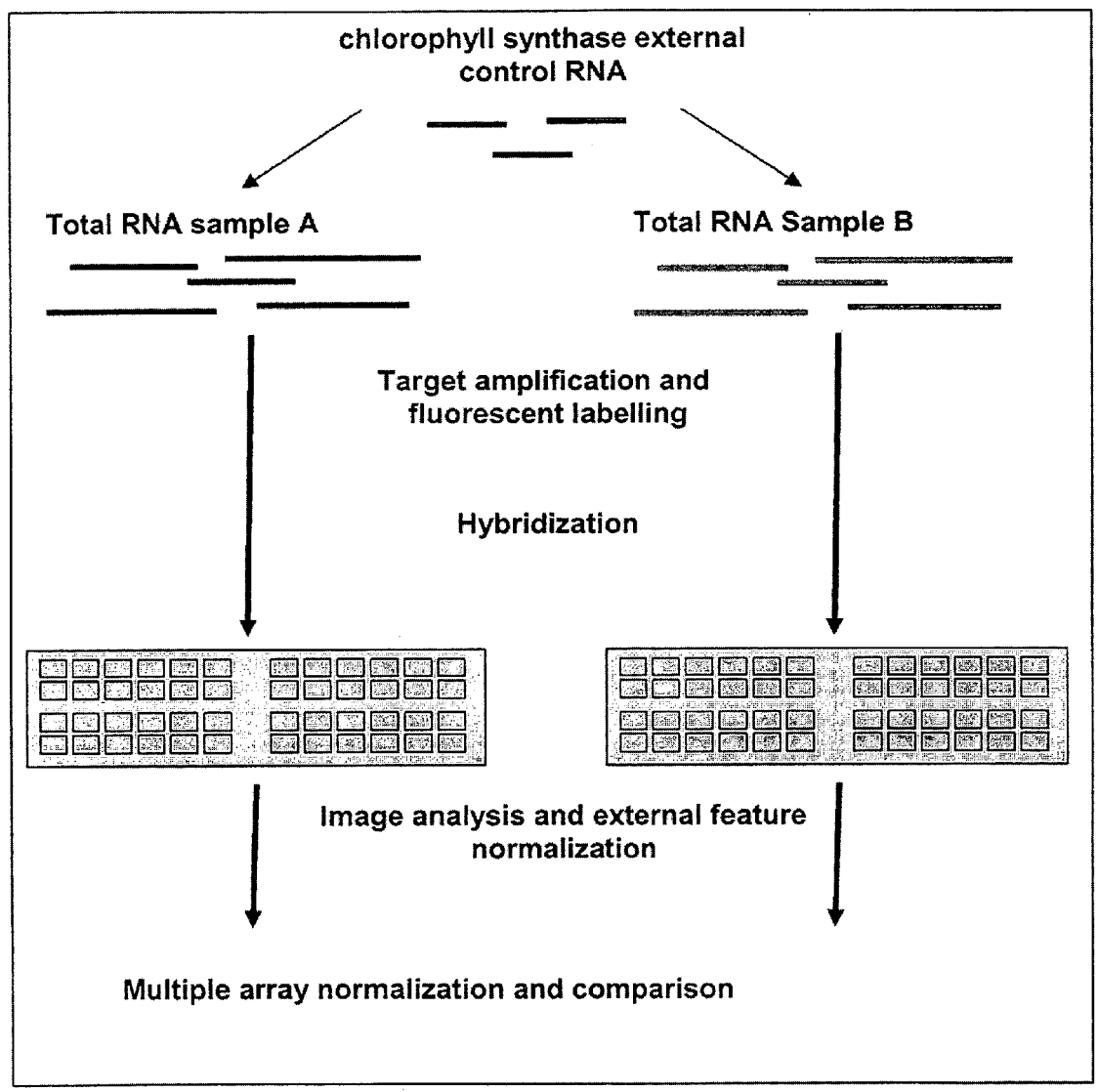
FIG. 10 shows the outline of an externally controlled microarray experiment.

The inventors have opted to add a constant quantity of external RNA to each total RNA sample while varying the amounts of external control oligo printed on the array (FIG. 10).

An oligo probe was designed for the *Arabidopsis thaliana* chlorophyll synthase gene.

External control target RNA was prepared through in vitro transcription of *A. thaliana* chlorophyll synthase cDNA present in a plasmid provided by the Ontario Cancer Institute. The chlorophyll synthase target RNA is added into the mouse target RNA, labeled with a fluorescent dye, and hybridized to the array. All methods followed are methods known in the art.

External control features of different concentrations will produce spots with different intensities as a result of hybridization of the external target RNA to the oligo content in the spot.

5. Optimization of External Control Oligo Dilution Series

Figure 11:
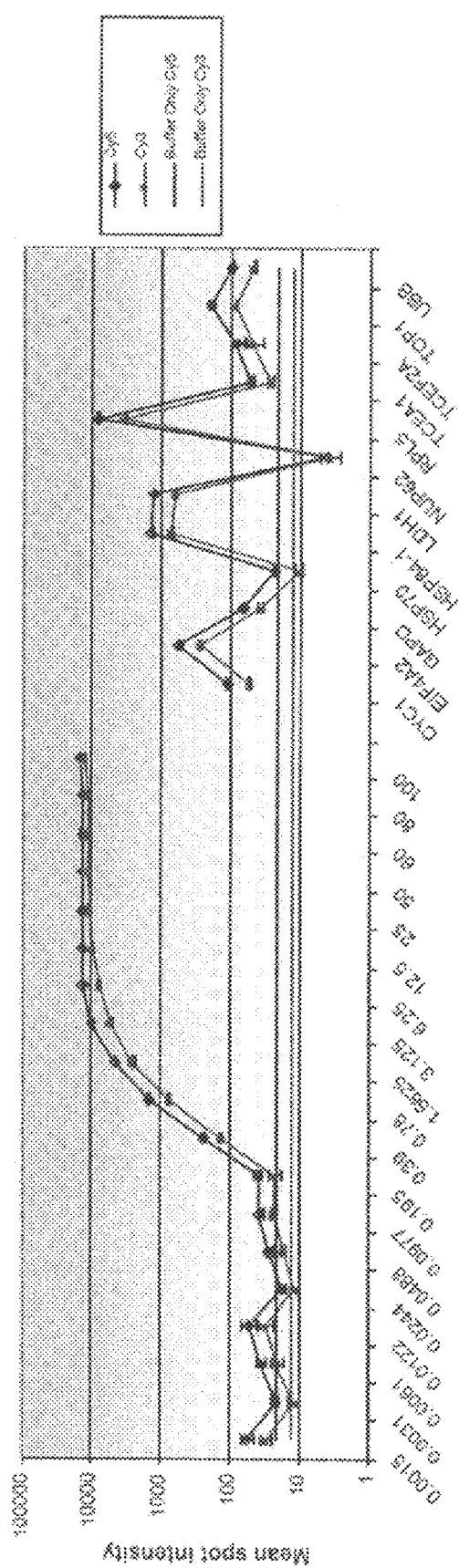
FIG. 11 shows the mean signal intensities of external control dilutions and test oligo features.
Figure 12:
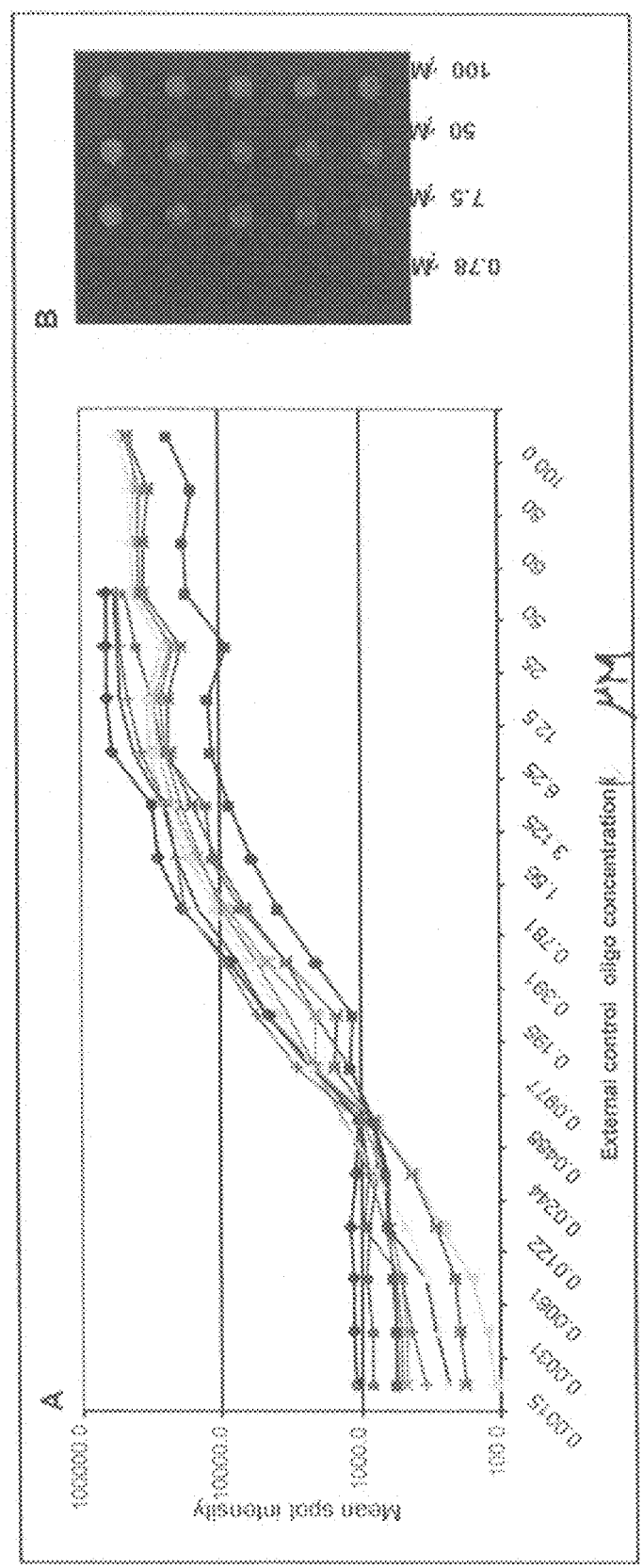
FIG. 12 shows the external control dilution series spot intensities. A shows the logarithmic plot of external dilution series spot intensities for 5 independent microarray experiments (Cy5 and Cy3). B shows a subset of external control features from a typical microarray image.

Microarrays were printed with external control oligo dilutions ranging from 100 µM to 0.0015 µM. External control RNA was spiked into reference RNA (Stratagene) prior to labelling. 2 ng, 8 ng, 18 ng, 20 ng, and 40 ng external control RNA spikes were tested. A series of 19 external control dilutions was found to be optimal, covering the complete range of expression levels observed for the test oligo set. (FIG. 11) and reproducible across experiments (FIG. 12).

6. Microarray Feature Printing Design

Systematic errors arising reproducibly as a result of experimental procedure contribute to inaccuracies in measured gene expression levels.

Figure 13:
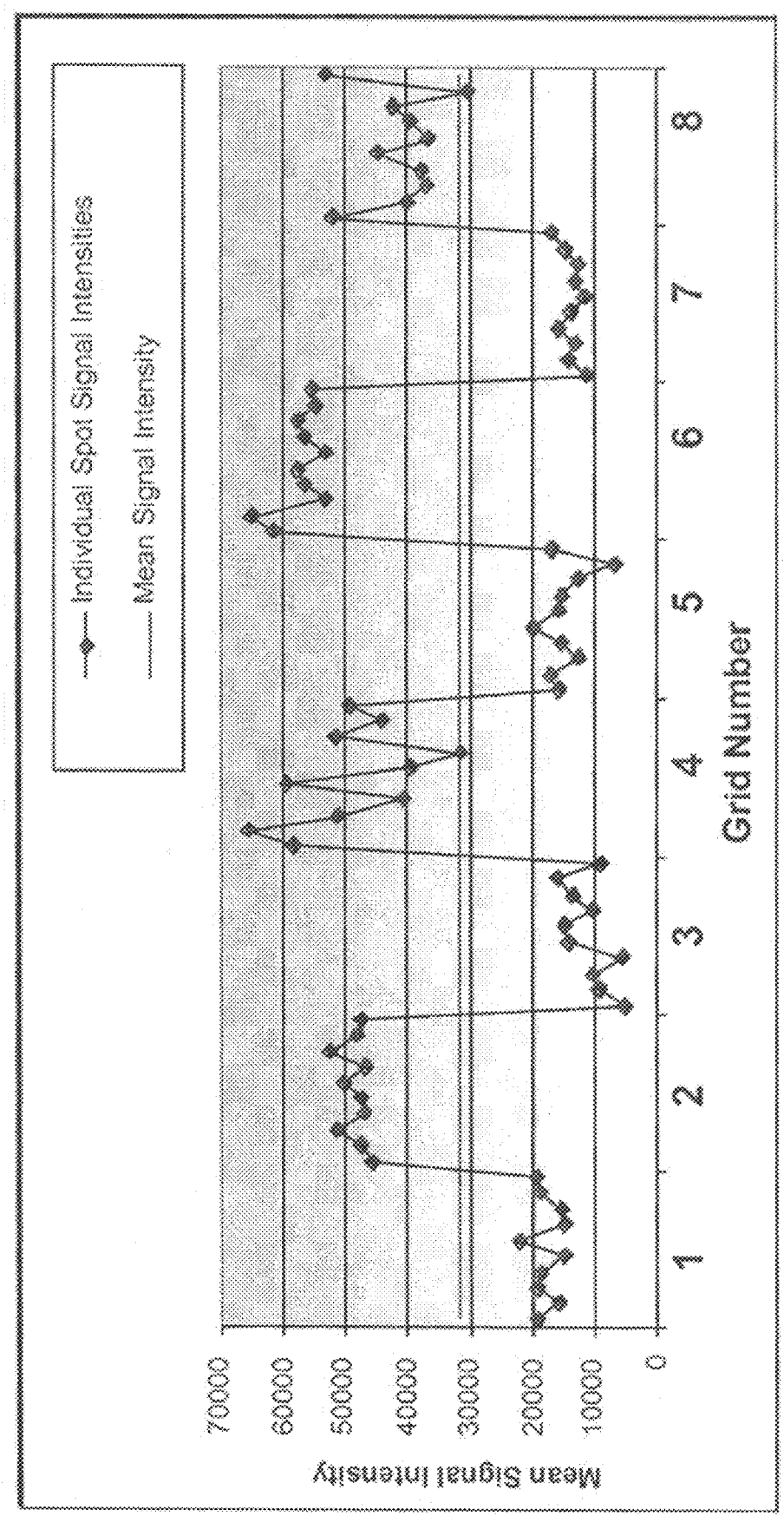
FIG. 13 shows signal intensities for a single external control dilution sorted by array grid position.

The spatial arrangement of features on a microarray resulting from printing design is one of the major sources of systematic error:

In FIG. 13 the spatial periodicity of spot intensity based on array grid position is evident.

Figure 14:
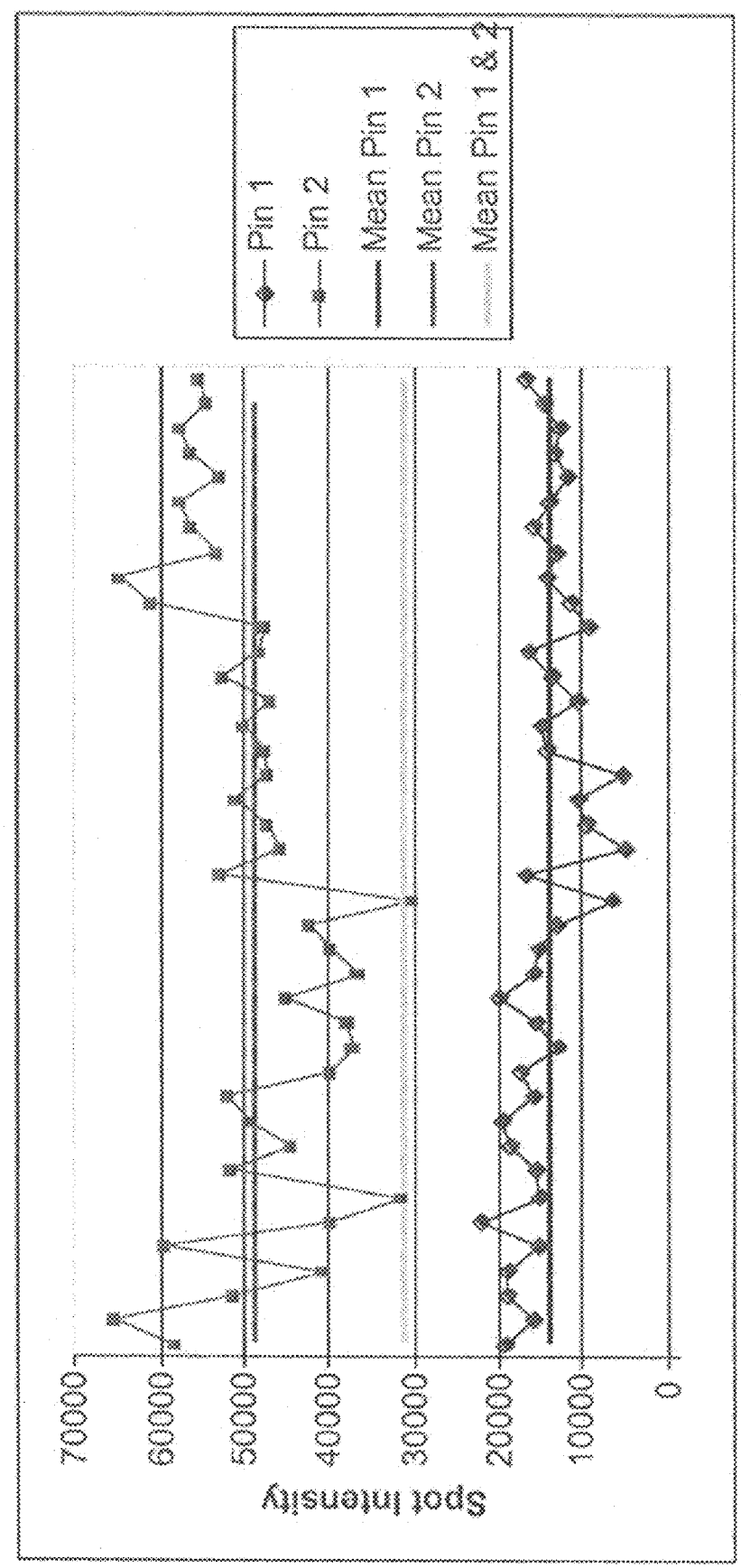
FIG. 14 shows signal intensities for a single external control dilution sorted by printing pin.

When the same data is sorted by printing pin (FIG. 14), a clear difference in spot intensity for the same feature is observed based on printing pin.

The TOXARRAY® has been designed such that all control and external normalization features are printed by each pin resulting in their presence in every grid on the array.

Each grid on the TOXARRAY® is printed in quadruplicate over the array area to account for within-slide spatial variations.

Each grid consists of 96 unique gene features and an identical layout of control features (FIG. 1) including:
- external control dilutions
- RpL5 housekeeping gene
- negative controls (buffer-only and randomized 70mers).

7. Quality Test

As can be appreciated from FIG. 2, by starting at extremely low molarity and going up to saturation, the inventors span the linear dynamic range of the signal intensities, allowing the choice of one or several spots to use within each subgrid for normalizing.

Figure 15:
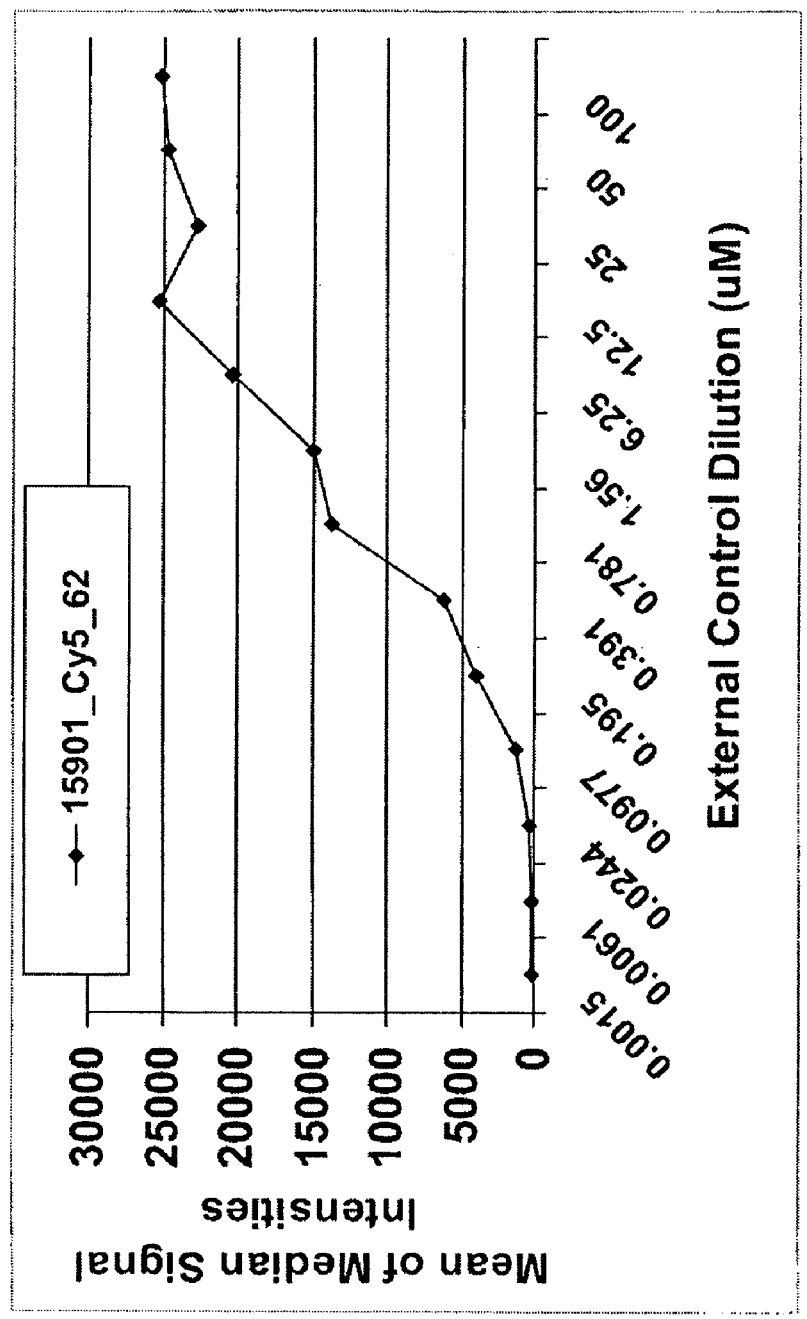
FIG. 15 shows a linear plot of external control dilution series.
Figure 16:
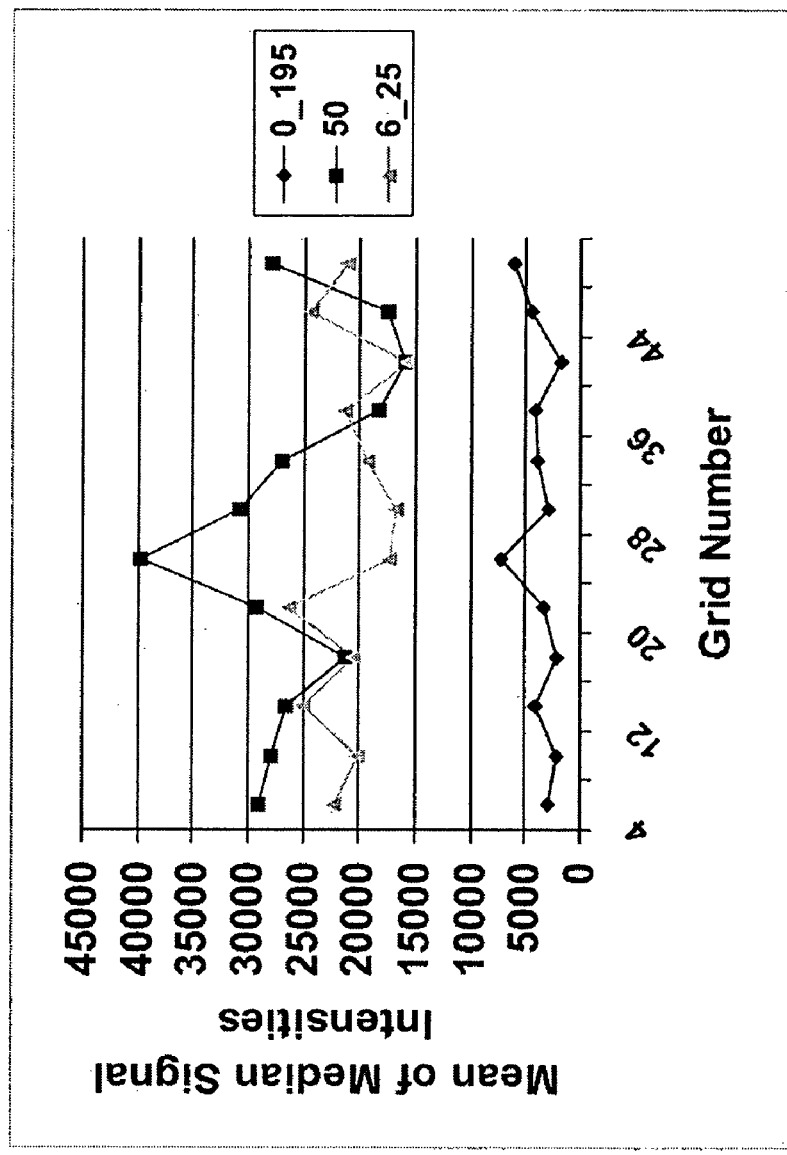
FIG. 16 shows replicate external control spots sorted by grid and metacolumn.

FIG. 15 shows the result from a recent quality test of the inventors TOXARRAY® plotting an external control dilution series, ensuring that within a subgrid one is spanning the range of signal intensities from background to saturation. This allows to choose an appropriate spot or two within each subgrid to normalize grids from top to bottom. As can be appreciated from FIG. 16, the system can thus can be used to simply detect differential hybridization (increasing grid number is going down the chip—if the line is sloping down or up, it indicates signal intensity of the same spot differs from top to bottom of the chip).

The inventors have thus designed an oligonucleotide-based microarray representing more than 1100 genes predictive of toxicant exposure based on gene expression data in current literature, in house data, and statistical re-analysis of relevant existing microarray data in which an external control feature for normalization has been designed and tested for its ability to mimic the range of observed expression levels for a test set of oligos. The individual grid layout and number of control and external normalization features per grid have been designed to cope with sources of both systematic error and spatial variation.

What is claimed is:

1. An array system comprising:
   a solid support having at least one grid attached thereto;
   at least one external control probe, said at least one external control probe being attached to at least one grid of said solid support in a series of, said series of differing amounts being applied randomly and evenly across an area of said at least one grid;
   a binding mixture containing a single amount of at least one external control target being complementary to said at least one external control probe; and
   a plurality of sample probes attached to said solid support at discrete locations among the layout of the series of differing amounts of the at least one external control probe.

2. The array system according to claim 1, wherein the binding mixture further comprises a plurality of sample targets that bind to the plurality of sample probes.

3. The array system according to claim 1, wherein the at least one external control probe and the sample probes are selected from the group consisting of DNA, RNA, oligonucleotides, cDNA, proteins and antibodies.

4. The array system according to claim 1, wherein said series of differing amounts of the at least one external control probe arises from spotting mixture concentrations varying from 0.0015 to 100 µM.

5. The array system according to claim 4, wherein said series of differing amounts of the at least one external control probe arises from spotting mixture concentrations of 0.0015, 0.0031, 0.0061, 0.0122, 0.0244, 0.0488, 0.0977, 0.195, 0.39, 0.78, 1.5625, 3.125, 6.25, 12.5, 25, 50, 60, 80 and 100 µM.

6. The array system according to claim 1, wherein the sample probes are oligonucleotides.

7. The array system according to claim 6, wherein the oligonucleotides are 70mer oligonucleotides.

8. The array system according to claim 7, wherein the 70mer oligonucleotides are designed and synthesized according to the following characteristics:
less than 60% G C content;
less than 1000 bases from the 3' end, the 3' end being the last base of a sequence matching a consensus polyadenylation signal sequence in an mRNA target;
longest stem being less than 9 bases, the stem being within the oligonucleotide; and less than 70% cross homology to sequences of target molecules in an intended sample to which the oligonucleotide is not intended to bind.

9. The array system according to claim 8, wherein the 70 mer oligonucleotides are attached to the solid support in amounts arising from spotting mixture concentrations of 60, 40, 30, 15, 7.5 and 3.5 µM.

10. The array system according to claim 9, wherein the 70mer oligonucleotides are attached to the solid support in an amount arising from a spotting mixture concentration of 40 µM.

11. The array system according to claim 1, wherein it is a microarray system.

12. The array system according to claim 1, wherein said at least one external control probe and said plurality of sample probes are printed on said solid support.

13. A process of normalizing an array system, comprising the steps of:
a) providing a solid support comprising at least one grid attached thereto;
b) attaching at least one external control probe to said solid support in a series of differing amounts, said series of differing amounts of said at least one external control probe being attached to the at least one grid of said solid support at known locations in a pre-determined layout but spatially randomized within the layout in said at least one grid;
c) attaching a plurality of sample probes to the at least one grid of said solid support at discrete locations among the layout of the series of differing amounts of the at least one external control probe;
d) binding a binding mixture to the array system, wherein the binding mixture comprises a plurality of sample targets and at least one external control target being complementary to said at least one external control probe;
e) measuring the level of binding between the at least one external control probe and the at least one external control target and between the plurality of sample probes and the plurality of sample targets; and
f) determining the amount of the plurality of sample targets present in the binding mixture.

14. The process according to claim 13, further comprising the following step:
g) attaching said series of differing amounts of said at least one external control probe in duplicate on said at least one grid.

15. The process according to claim 13, further comprising at least one of the following steps:
h) adding a buffer only to at least a discrete spot on said at least one grid;
i) leaving at least one empty discrete spot in said at least one grid;
j) attaching a random hexamer to one spot on said at least one grid;
k) attaching a random pool of 70mer oligonucleotides to at least one discrete spot on said at least one grid; and
l) attaching a probe from a house keeping gene to at least one discrete spot on said at least one grid.

16. The process according to claim 15, wherein the house keeping gene is RpL5.

17. The process according to claim 15, further comprising the step of:
m) attaching a plurality of sample probes in other discrete spots of each said at least one grid.

18. The process according to claim 13, wherein the binding mixture comprises a plurality of sample targets that bind to the plurality of sample probes.

19. The process according to claim 13, wherein the at least one external control probe and the plurality of sample probes are selected from the group consisting of DNA, RNA, oligonucleotides, cDNA, proteins and antibodies.

20. The process according to claim 13, wherein said series of differing amounts of the at least one external control probe arise from spotting mixture concentrations varying from 0.0015 to 100 µM.

21. The process according to claim 20, wherein said series of differing amounts of the at least one external control probe arise from spotting mixture concentrations of 0.0015, 0.0031, 0.0061, 0.0122, 0.0244, 0.0488, 0.0977, 0.195, 0.39, 0.78, 1.5625, 3.125, 6.25, 12.5, 25, 50, 60, 80 and 100 µM.

22. The process according to claimed 13, wherein the sample probes are oligonucleotides.

23. The process of according to claim 22, wherein the oligonucleotides are 70mer oligonucleotides.

24. The process according to claim 23, wherein the 70mer oligonucleotides are designed and synthesized according to the following characteristics:
less than 60% G C content;
less than 1000 bases from the 3' end, the 3' end being the last base of a sequence matching a consensus polyadenylation signal sequence in an mRNA target;
longest stem being less than 9 bases, the stem being within the oligonucleotide; and
less than 70% cross homology to sequences of target molecules in an intended sample to which the oligonucleotide is not intended to bind.

25. The process according to claim 24, wherein the 70 mer oligonucleotides are attached to the solid support in amounts arising from spotting mixture concentrations of 60, 40, 30, 15, 7.5 and 3.5 µM.

26. The process according to claim 25, wherein the 70mer oligonucleotides are attached to the solid support in an amount arising from a spotting mixture concentration of 40 µM.

27. A kit, comprising:
a solid support having at least one grid attached thereto;
at least one external control probe, said at least one external control probe being attached to at least one grid of said solid support in a series of differing amounts, said series of being applied randomly and evenly across an area of said at least one grid;
a binding mixture containing a single amount of at least one external control target being complementary to said at least one external control probe; and
a plurality of sample probes attached to said solid support at discrete locations among the layout of the series of differing amounts of the at least one external control probe.

28. The kit according to claim 27, wherein the binding mixture further comprises a plurality of sample targets that bind to the plurality of sample probes.

29. The kit according to claim 28, wherein the at least one external control probe and the sample probes are selected from the group consisting of DNA, RNA, oligonucleotides, cDNA, proteins and antibodies.

30. The kit according to claim 29, wherein said series of differing amounts of the at least one external control probe arises from spotting mixture concentrations varying from 0.0015 to 100 µM.

31. The kit according to claim 30, wherein said series of differing amounts of the at least one external control probe arise from spotting mixture concentrations of 0.0015, 0.0031, 0.0061, 0.0122, 0.0244, 0.0488, 0.0977, 0.195, 0.39, 0.78, 1.5625, 3.125, 6.25, 12.5, 25, 50, 60, 80 and 100µM.

32. The kit according to claim 31, wherein the sample probes are oligonucleotides.

33. The kit according to claim 32, wherein the oligonucleotides are 70mer oligonucleotides.

34. The kit according to claim 33, wherein the 70mer oligonucleotides are designed and synthesized according to the following characteristics:
less than 60% G C content;
less than 1000 bases from the 3' end, the 3' end being the last base of a sequence matching a consensus polyadenylation signal sequence in an mRNA target;
longest stem being less than 9 bases, the stem being within the oligonucleotide; and
less than 70% cross homology to sequences of target molecules in an intended sample to which the oligonucleotide is not intended to bind.

35. The kit according to claim 33, wherein the 70mer oligonucleotides are attached to the solid support in amounts arising from spotting mixture concentrations of 60, 40, 30, 15, 7.5 and 3.5 µM.

36. The kit according to claim 35, wherein the 70mer oligonucleotides are attached to the solid support in amounts arising from a spotting mixture concentration of 40 µM.

* * * * *